United States Patent
Jagdeo et al.

(10) Patent No.: US 9,861,832 B2
(45) Date of Patent: Jan. 9, 2018

(54) METHODS FOR IN VITRO INHIBITION OF FIBROBLAST PROLIFERATION

(71) Applicants: THE REGENTS OF THE UNIVERSITY OF CALIFORNIA, Oakland, CA (US); THE RESEARCH FOUNDATION OF STATE UNIVERSITY OF NEW YORK, Albany, NY (US)

(72) Inventors: Jared Jagdeo, Brooklyn, NY (US); Roslyn Rivkah Isseroff, Sacramento, CA (US); Andrew Mamalis, Sacramento, CA (US); Neil Brody, Manhasset, NY (US); Daniel Siegel, St. James, NY (US); Hadar Lev-Tov, Sacramento, CA (US)

(73) Assignees: THE REGENTS OF THE UNIVERSITY OF CALIFORNIA, Oakland, CA (US); THE RESEARCH FOUNDATION OF STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 14/207,114

(22) Filed: Mar. 12, 2014

(65) Prior Publication Data
US 2014/0277293 A1    Sep. 18, 2014

Related U.S. Application Data

(60) Provisional application No. 61/777,854, filed on Mar. 12, 2013.

(51) Int. Cl.
A61N 5/06 (2006.01)

(52) U.S. Cl.
CPC .... *A61N 5/0616* (2013.01); *A61N 2005/0651* (2013.01); *A61N 2005/0659* (2013.01); *A61N 2005/0663* (2013.01)

(58) Field of Classification Search
CPC ............... A61N 5/0613; A61N 5/0616; A61N 2005/0658; A61N 2005/0659; A61N 2005/0662; A61N 2005/0663
USPC .......................................................... 607/88
See application file for complete search history.

(56) References Cited

U.S. PATENT DOCUMENTS

| | | | |
|---|---|---|---|
| 7,094,252 B2 * | 8/2006 | Koop | 607/88 |
| 2003/0004556 A1 * | 1/2003 | McDaniel | 607/88 |
| 2003/0171795 A1 * | 9/2003 | Walmsley et al. | 607/88 |
| 2006/0241726 A1 * | 10/2006 | Whitehurst | 607/86 |

(Continued)

OTHER PUBLICATIONS

Favero et al., Low-Level Laser Irradiation (InGaAlP-660 nm) Increases Fibroblast Cell Proliferation and Reduces Cell Death in a Dose-Dependent Manner, 2009, Photomedicine and Laser Surgery, vol. 00, No. 00.*

(Continued)

*Primary Examiner* — John R Downey
(74) *Attorney, Agent, or Firm* — O'Banion & Ritchey LLP; John P. O'Banion

(57) ABSTRACT

Methods for LED generated low-level light therapy (LLLT) in the red, blue, and IR ranges are described to effectively inhibit fibroblast proliferation in vitro without altering viability, and may be used as therapy for the treatment of scars and other proliferative skin diseases.

19 Claims, 8 Drawing Sheets

(56) References Cited

U.S. PATENT DOCUMENTS

2009/0054953 A1* 2/2009 Whitehurst ............... 607/88
2009/0163819 A1* 6/2009 De Kok et al. ............ 600/476

OTHER PUBLICATIONS

Loevschall et al., Effect of Low Level Diode Laser Irradiation of Human Oral Mucosa Fibroblasts in Vitro, 1994, Lasers in Surgery and Medicine, 14:347-354.*
Young et al., Macrophase Responsiveness to Light Therapy, 1989, Lasers in Surgery and Medicine, 9:497-505.*
Vinck, E., et al. "Increased fibroblast proliferation induced by light emitting diode and low power laser irradiation," Lasers Med Sci (2003) 18: pp. 95-99.
PR News Channel, "New Tampa, Fla. manufacturer launches deep UV LED medical device for treating psoriasis, eczema, vitiligo," http://www.prnewschannel.com/2011/08/11/new-tampa-fla-manu-facturer-launches-deep-uv-led-medical-device-for-treating-psoriasiseczema-vitiligo/ (2011) pp. 1-2.
Esmaeelinejad, M., et al., "The effects of low-level laser irradiation on cellular viability and proliferation of human skin fibroblasts cultured in high glucose mediums," Lasers Med Sci (2014), published online Mar. 2, 2013, 29:121-129.

* cited by examiner

METHODS FOR IN VITRO INHIBITION OF FIBROBLAST PROLIFERATION

CROSS-REFERENCE TO RELATED APPLICATIONS

This application claims the benefit of U.S. provisional patent application Ser. No. 61/777,854 filed on Mar. 12, 2013, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to treatment of skin tissue, and more particularly to in vivo tissue treatment via light therapy.

2. Description of Related Art

Red light and blue light are part of the visible light spectrum. The effects of light emitting diode (LED) generated red and blue light on human skin are not well characterized.

The photobiomodulatory properties of ultraviolet light have been well characterized in previous studies; however, the photobiomodulatory effects of light in the visible spectrum, which accounts for 40-45% of solar energy, are not well defined. Visible daylight (approximately 400 nm-700 nm) is considered to have minimal deleterious effects on human skin and is therefore relatively safe. Red light is part of the visible light spectrum and its effects on human skin have been studied in the context of laser light sources but little is known about the effects of LED generated red light on normal human skin. Blue light is also part of the visible light spectrum and its effects on human skin are not well documented.

Low level light therapy (LLLT) typically involves applying light in the red to near infrared spectrum in order to photo-stimulate or photo-inhibit the cytochrome C component of the electron transport chain. This photobiomodulatory effect is thought to be mediated by the heme-copper photoacceptors within cytochrome C and results in alteration of cellular properties.

Scars, including hypertrophic scars and keloids, represent a significant clinical burden worldwide that affects many skin types. There are a variety of treatment options for scars and each is associated with various benefits, safety profile, adverse events, financial and time considerations.

Pre-clinical research of scars is especially challenging due to inadequate animal models which limits our understanding of its pathogenesis.

Accordingly, an object of the present invention is to develop more efficacious treatment options with a minimal risk profile.

BRIEF SUMMARY OF THE INVENTION

An aspect of the present invention is LED generated low-level light therapy (LLLT) in the red, blue, and infrared (IR) ranges for inhibition of fibroblast proliferation and viability in vitro.

At certain fluences, red, blue and IR LLLT can effectively inhibit fibroblast proliferation in vitro without altering viability, and may be used as therapy for the treatment of scars and other proliferative skin diseases.

A principle discovery of the present invention is that light emitting diode (LED) generated light at the appropriate fluences/doses can inhibit fibroblast proliferation and alter key characteristics of normal and pathologic keloid scar derived skin fibroblast cells. These results are unexpected, as they go against the general understanding in the art that low-level light therapy can increase fibroblast proliferation. (See Esmaeelinejad M, et al. *The Effects of Low-level Laser Irradiation on Cellular Viability and Proliferation of Human Skin Fibroblasts Cultured in High Glucose Mediums.* Lasers, Med Sci. 2014 January; 29(1):121-9).

Since there are few effective treatment options for keloids and other cutaneous fibrotic diseases, the methods of the present invention may be particularly advantageous for use in LED-based red, blue and infrared light management of keloid scars and other scarring (fibrotic) skin diseases.

We demonstrate that certain doses (fluences) of red, blue or infrared light generated by LED can modulate, in vitro, skin cell functions associated with scarring conditions known as skin fibrosis.

LED generated red, blue and infrared light phototherapy of skin fibrosis (scars) has several advantages over alternate ways of skin scarring treatment. LED generated red and infrared light phototherapy is: 1) non-invasive, 2) low cost, 3) safe for patient use at home, 4) portable, 5) easy to use, 6) small/handheld size, and 7) can be combined with other anti-fibrotic skin therapies.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
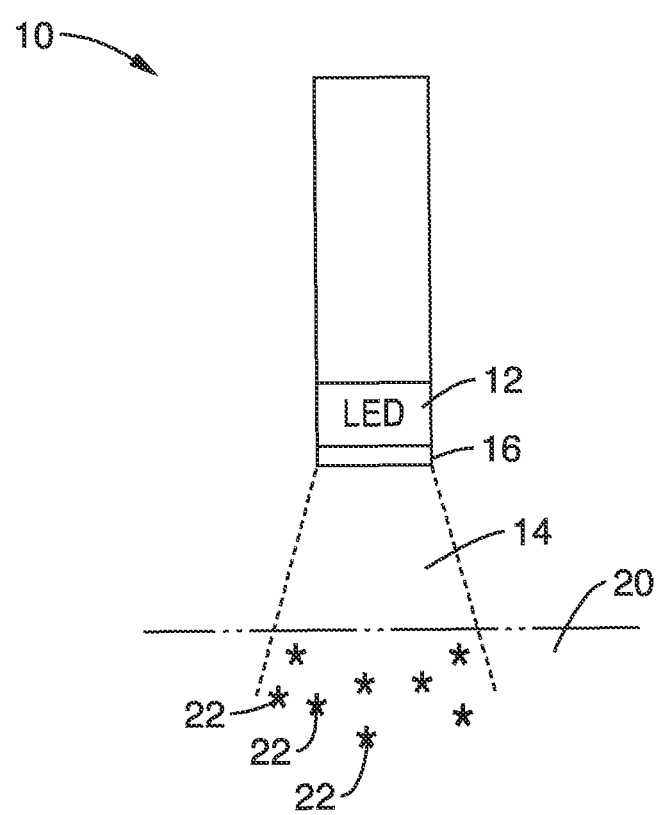
FIG. 1 is a schematic diagram of an LED device being used to provide in vitro light therapy to inhibit fibroblast proliferation in skin tissue.

FIG. 1 shows a schematic diagram of a low-light therapy device 10 configured for inhibition of fibroblast proliferation within tissue in accordance with the present invention. Device 10 comprises a light emitting diode (LED) 12 that is configured to direct light 14 into a region of tissue 20 to modify proliferation of fibroblasts 22 located within the tissue site 20. Light 14 may be in the red, IR, and blue light ranges, and is emitted at a density configured to inhibit proliferation. LED 12 may comprise one or a plurality of LEDs that are directed to create beam 14.

Beam 14 may be focused or collimated depending on the desired intensity or path for therapy. Light beam 14 may be emitted at a wavelength corresponding to red, blue, or IR light bands. This may be achieved via LEDs 12 configured for a particular selected wavelength, a filter 16 may be used to filter the beam 14 to a desired wavelength.

The beam 14 is transmitted into tissue 20 at an intensity/duration resulting in a light fluence/dose configured to inhibit fibroblast proliferation. For red light (e.g. at 633 nm) and IR light (e.g. at 830 nm), fluences of at least 30 J/cm$^2$, and preferably 160 J/cm$^2$, 320 J/cm$^2$, 640 J/cm$^2$, or over 800 J/cm$^2$ are desired. For blue light, fluences as low as of 5 J/cm$^2$, but preferably greater than 10 J/cm$^2$, are preferred. In some instances, the upper limit for light density is a result of practical limitations such as the duration of therapy a patient is comfortable with given the output of the LEDs.

Experimental Results

In a first experiment, irradiation of normal human skin fibroblasts using red LED panels was performed in vitro, and modulation of proliferation and viability was quantified by trypan blue dye exclusion assay.

Monolayers of normal human skin fibroblasts (AG13145 strain, Coriell Institute for Medical Research, Camden, New Jersey) were cultured in Dulbecco's Modified Eagle Medium (Gibco/ Invitrogen, Carlsbad, Calif.) with 15% bovine calf serum (Atlanta Bio, Lawrenceville, Ga.) and 1% penicillin, streptomycin and neomycin antibiotic mixture (Gibco). The cell cultures were incubated at 37° C. with 5% $CO_2$. Fibroblasts seeded at 2×10$^4$ cells per 35 mm dish were irradiated 24 hours after passaging, using a 633 nm light emitting diode array (Omnilux new-U, courtesy of Photo Therapeutics, Carlsbad, Calif.) at power density of 872.6 W/m$^2$ at room temperature. Media temperatures measured throughout irradiations remained under 37° C. By remaining within physiological temperatures, heat stress was not induced. After 48 hours of additional incubation, the cells were harvested, counted and assessed for viability as determined by Trypan blue exclusion assay.

The amount of cells in suspension was determined by sampling a specific volume and then counting the cells using a hemocytometer that is visualized using light microscopy. The number of cells counted was used to quantify the total number of cells suspended in the original population. Dead cells have porous cell membranes that allow for intracellular penetration of the trypan blue dye (visualized as blue cells using light microscopy). Therefore the trypan blue dye allows clear visualization of "live" and "dead" cells by "excluding" the dye from live cells with intact cell membranes. Viability was then calculated based upon the ratio of live (total minus dead) to total cells.

All experiments were repeated to verify data reproducibility and accuracy and identical trends were demonstrated in a second fibroblast cell population, primary neonatal foreskin cell line NHF 05-01 (data not shown). Each experimental plate receiving LED treatment was randomly matched with a "bench control plate" (BCP) in order to ensure the measured effect was a result of LED treatment and not incandescent light. BCPs were derived from the same stock of cell suspension. BCPs were taken out of the incubator at the same time as their matched treatment pairs. BCPs were then left on the bench for the same amount of time and in the same ambient environment as the treatment plates. BCPs were protected from the LED light source, and media temperatures measured throughout their duration on the bench remained under 37° C. Both treatment plates and BCPs were then returned to the incubator and processed according to the exact same protocol. Cell counts included all cells in the sample including media change, trypinization products and washes. Mean percent proliferation and viability (live cells/total (live+dead) cells) relative to non-irradiated controls, are reported as mean values±standard error of the mean (SEM). Statistical analysis was performed using analysis of variance (ANOVA) to compare treatment arms and student's T-test to compare each treatment arm to the paired control arm.

Experimental results demonstrate that treatment of normal human skin fibroblasts with LED-generated red light (633 nm) modulates proliferation without significant effect on viability at all fluences.

Figure 2:
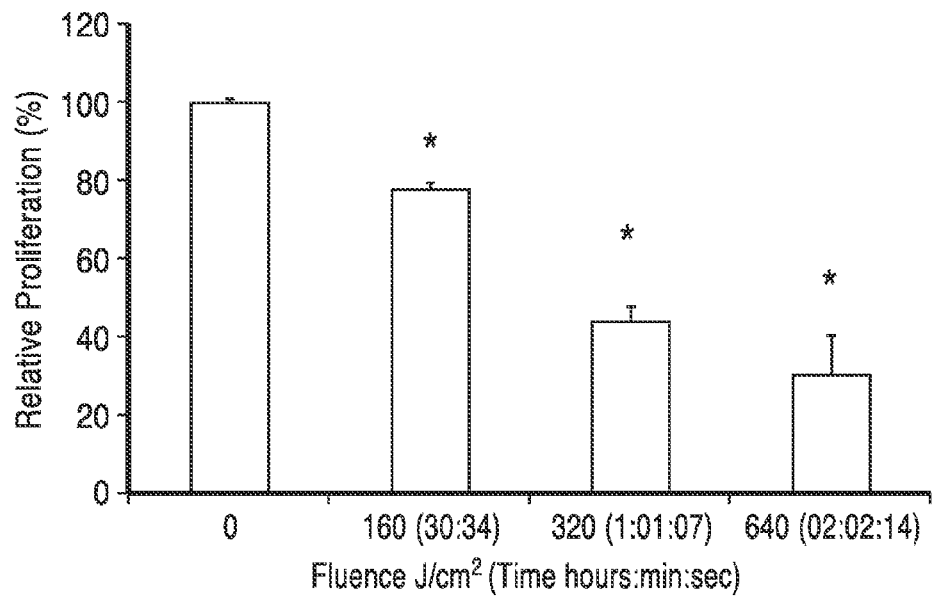
FIG. 2 is a plot showing the LED-Red Light (RL) effect on normal skin fibroblast proliferation.
Figure 3:
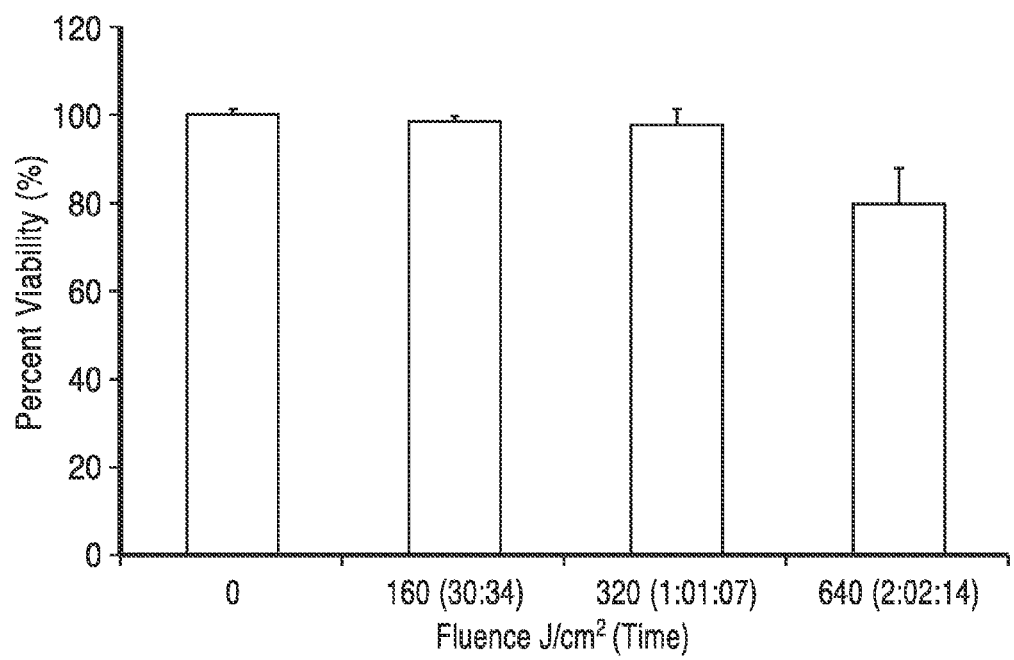
FIG. 3 is a plot showing the LED-RL effect on normal skin fibroblast viability.

Referring to the plot in FIG. 2, statistically significant decreases in cell proliferation are noted at the following fluences (time): 160 J/cm$^2$ (30 min: 34 sec), 320 J/cm$^2$ (61 min: 07 sec) and 640 J/cm$^2$ (122 min: 14 sec) (FIG. 1). As seen in FIG. 3, relative viability was not significantly altered by irradiation at the 160 J/cm$^2$, 320 J/cm$^2$ and 640 J/cm$^2$ doses (98.5±1.25% to 98.0±3.15%, 80.24±8.12% respectively) compared to the non-irradiated controls (FIG. 2). BCPs demonstrated decrease in proliferation for all fluences.

However, when compared to fluence matched BCPs, treatment plates demonstrated a 5.1% absolute percent decrease in proliferation for the lowest dose (160 J/cm$^2$; p=0.25), and for the higher doses a statistically significant decrease in proliferation compared to their corresponding BCP, resulting in absolute percent reduction of 31.5% (320 J/cm$^2$; p<0.01) and 43.3% 640 J/cm$^2$; p<0.01) (FIG. 2). Treatment with LED generated red light at a dose of 640

J/cm2 (122 min: 14 sec) resulted in a non-statistically significant decrease in viability compared to control and compared to BCP (FIG. 2).

Figure 4A:
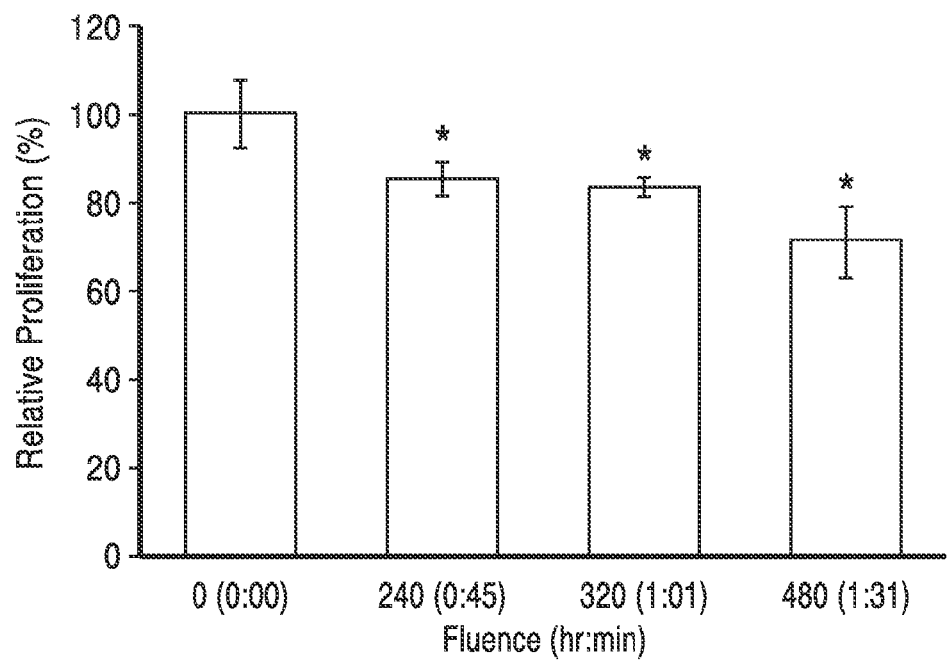
FIG. 4A and FIG. 4B are plots showing that LED-RL decreases keloid-scar derived fibroblast proliferation in two populations.
Figure 4B:
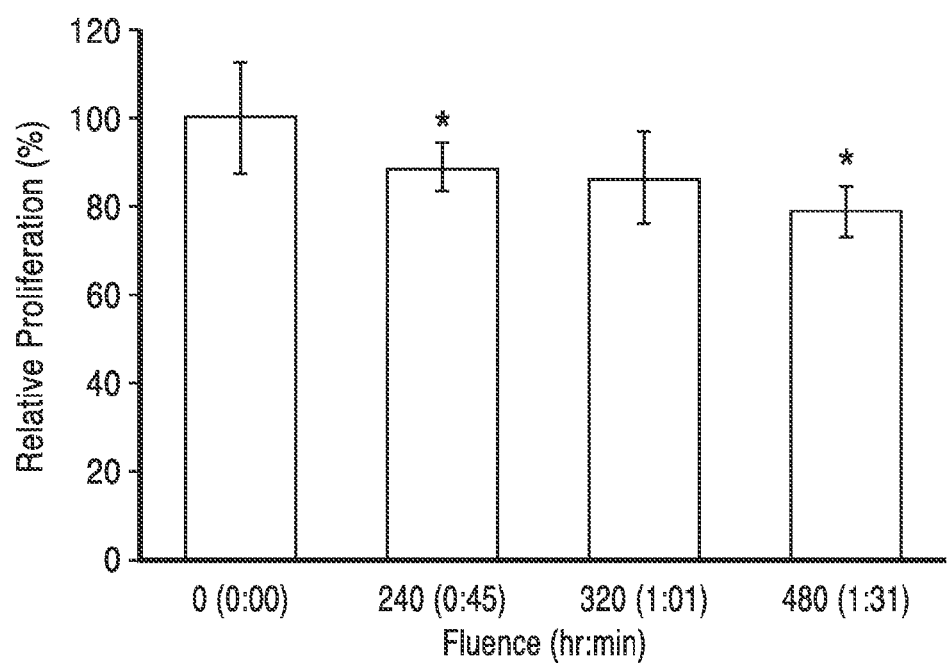

Referring to FIG. 4A and FIG. 4B, LED-based red light also decreases keloid-fibrotic scar tissue derived fibroblast cell proliferation in two different keloid-derived cultures from patient scars. In FIG. 4A, a 'KEL-MW3' culture showed inhibition of proliferation at 240 J/cm$^2$=85.1±3.77% p=0.015, 320 J/cm$^2$=83.54±2.19% p=0.003 and 480 J/cm$^2$=71.06±8.01% p=0.007. In FIG. 4B, a 'KEL-S' culture showed inhibition of proliferation at 240 J/cm$^2$=89.25±5.3% p=0.153, 320 J/cm$^2$=86.5±10.59% p=0.297, and 480 J/cm$^2$=79.03±5.95% p=0.032.

Figure 5:
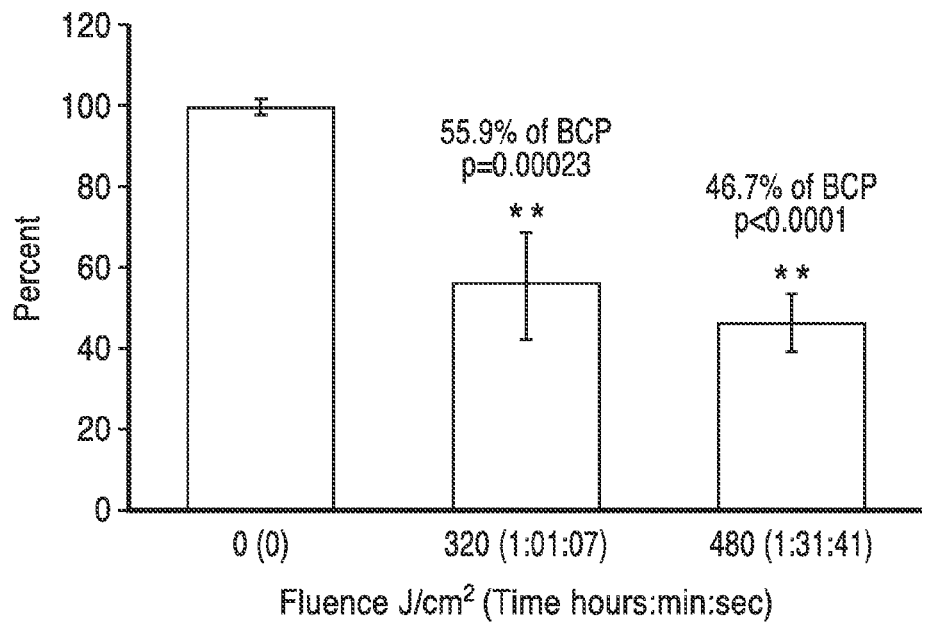
FIG. 5 is a plot showing that LED-RL irradiation twice daily decreases fibroblast proliferation more than a one-time treatment.

Experiments were also conducted to show results of low light therapy over several days. FIG. 5 shows a dosing study demonstrating that twice daily dosing, spread twelve hours apart, results in greater decrease in proliferation of normal fibroblast skin cells than one time dosing. The LED generated red light (633 nm) relative cell proliferation in vitro at various fluences was: 0 J/cm2=100 ±1.71%, 320 J/cm2=55.85 ±13.07%, 480 J/cm2=52.35 ±13.3%, 48-hours following irradiation. Proliferation is shown as percent of the control. Cells were irradiated with noted fluences four times over two days. Error bars represent standard error of the mean.

Figure 6:
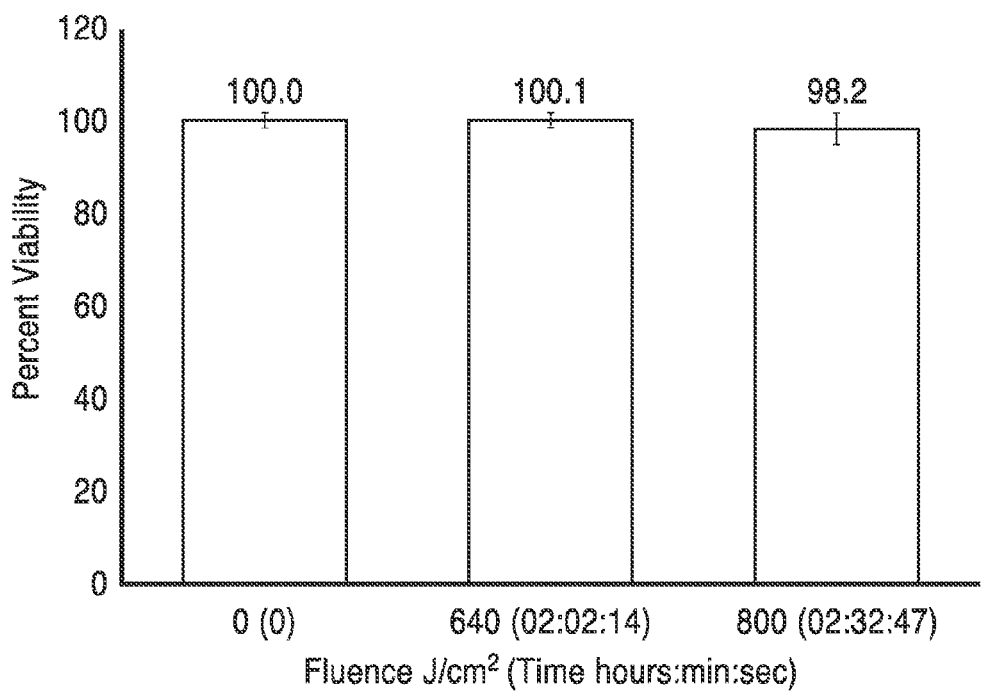
FIG. 6 is a plot showing effects of LED-RL on normal fibroblast viability in vitro for higher fluences (640 J/cm$^2$ and 800 J/cm$^2$).

FIG. 6 shows the effects of LED red light on normal fibroblast viability in vitro for larger fluences (640 J/cm$^2$ and 800 J/cm$^2$). Viability was shown not to be statistically impacted, even at higher fluences.

Figure 7:
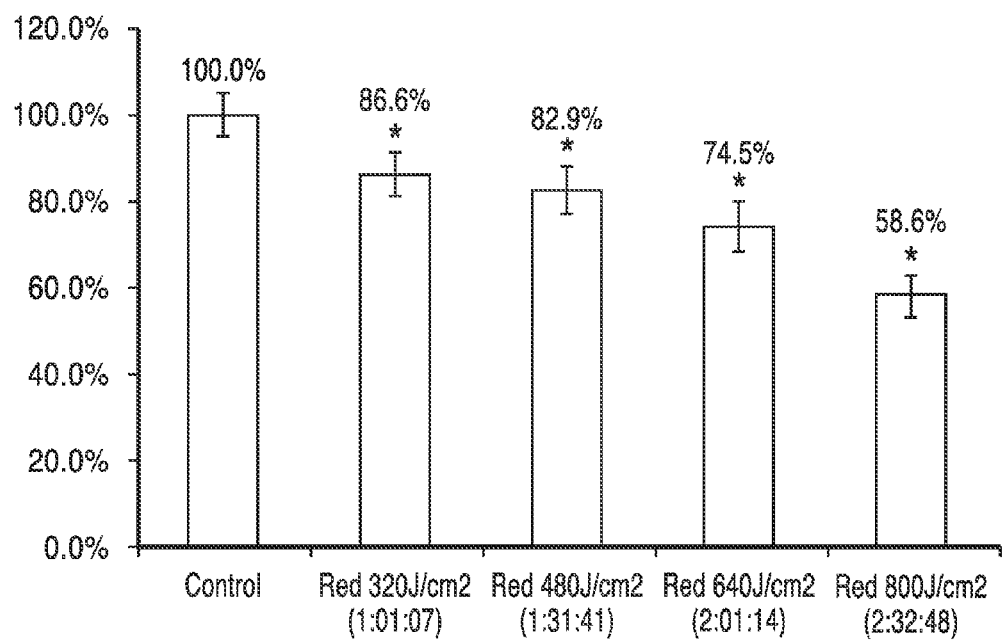
FIG. 7 is a plot showing that LED-RL decreases relative migration speed of fibroblasts in a dose-dependent manner.

FIG. 7 shows that LED red light decreases the relative migration speed of fibroblasts in a dose-dependent manner. Primary human fibroblasts were irradiated with increasing fluences of LED-RL. A bench control dish was incubated at the same temperature as the irradiated group for an equivalent amount of time. Post-exposure, cells irradiated with LED-RL demonstrated a significant decrease in migration speed compared to their matched bench control. Rates of cell migration are presented as relative percent speed of LED-irradiated cells compared with matched control ±percent SEM. Fluences of 320, 480, 640, and 800 J/cm2 decreased fibroblast migration speed to: 86.7% (0.337±0.02 versus bench control 0.389±0.02; p=0.0392), 83.0% (0.311±0.021 versus bench control 0.375±0.022; p=0.0395), 74.4% (0.269±0.02 versus bench control 0.361±0.015; p=0.000899, 58.6% (0.202±0.017 versus bench control 0.345±0.019; p=0.00000000003) of the bench control plate, respectively.

Figure 8A:
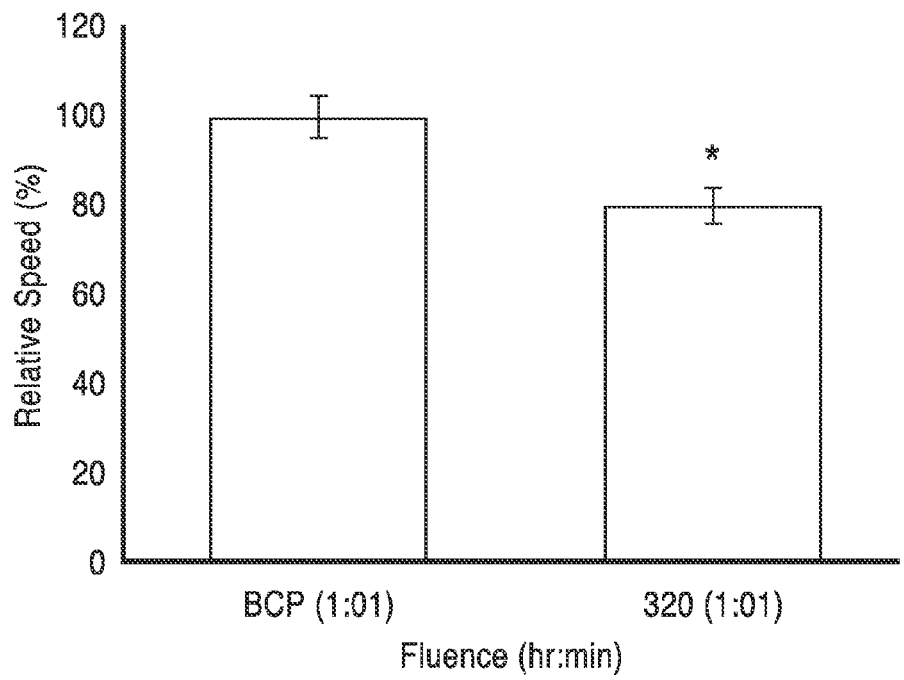
FIG. 8A and FIG. 8B are plots showing that LED-RL decreases migration speed of two keloid derived fibroblast cultures.
Figure 8B:
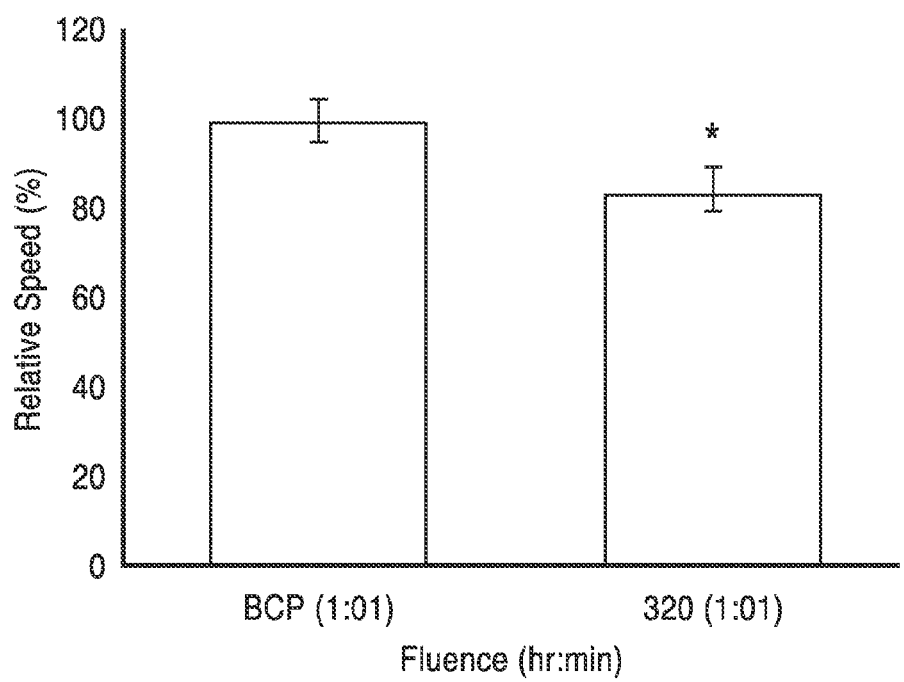

FIG. 8A and FIG. 8B shows LED-red light also decreases keloid-derived fibroblast migration speed as shown in two keloid-scar derived fibroblast populations. As shown in FIG. 8A, 'KEL-MW3' culture irradiation decreased speed by 19.58±3.88% (0.25±0.012 μm/min, p=0.005) versus BCP (0.311±0.015 μm/min). As shown in FIG. 8B, 'KEL-S' culture irradiation decreased speed by 14.97±4.68% (0.244±0.013 μm/min, p=0.023) versus BCP (0.287±0.013 μm/min).

Experiments were also conducted on the effects of low-level IR light on fibroblast proliferation and viability.

Figure 9:
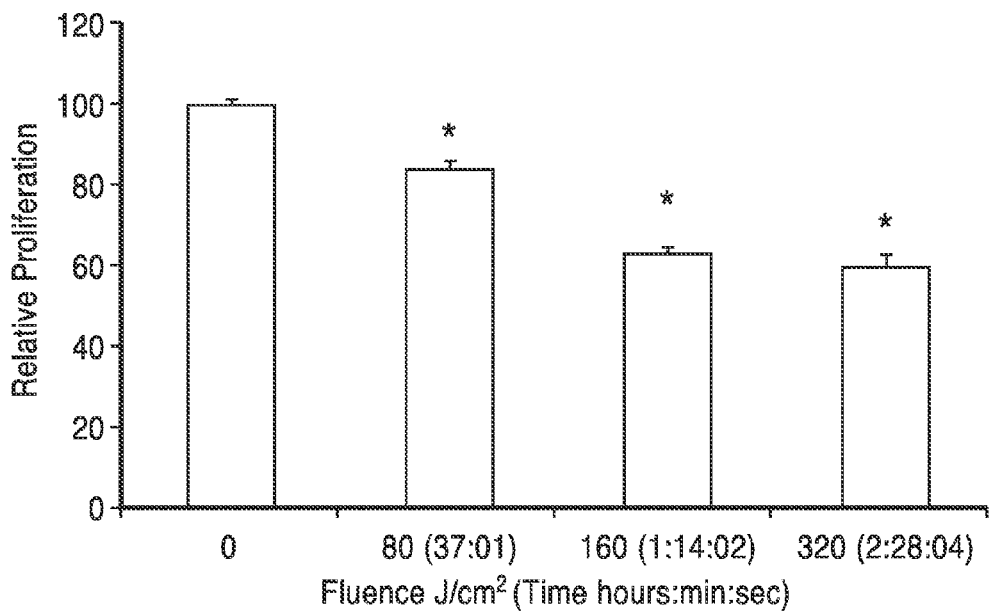
FIG. 9 is a plot showing the effect of LED-Infrared (IR) light on normal human skin fibroblast proliferation.

FIG. 9 shows that light-emitting-diode (LED)-generated infrared (IR) light (830 nm) induces statistically significantly less proliferation of normal human skin fibroblasts at fluences of 80 J/cm$^2$ (82.9±2.1%), 160 J/cm$^2$ (63.1±2.0%), and 320 J/cm$^2$ (58.6±1.7%).

Figure 10:
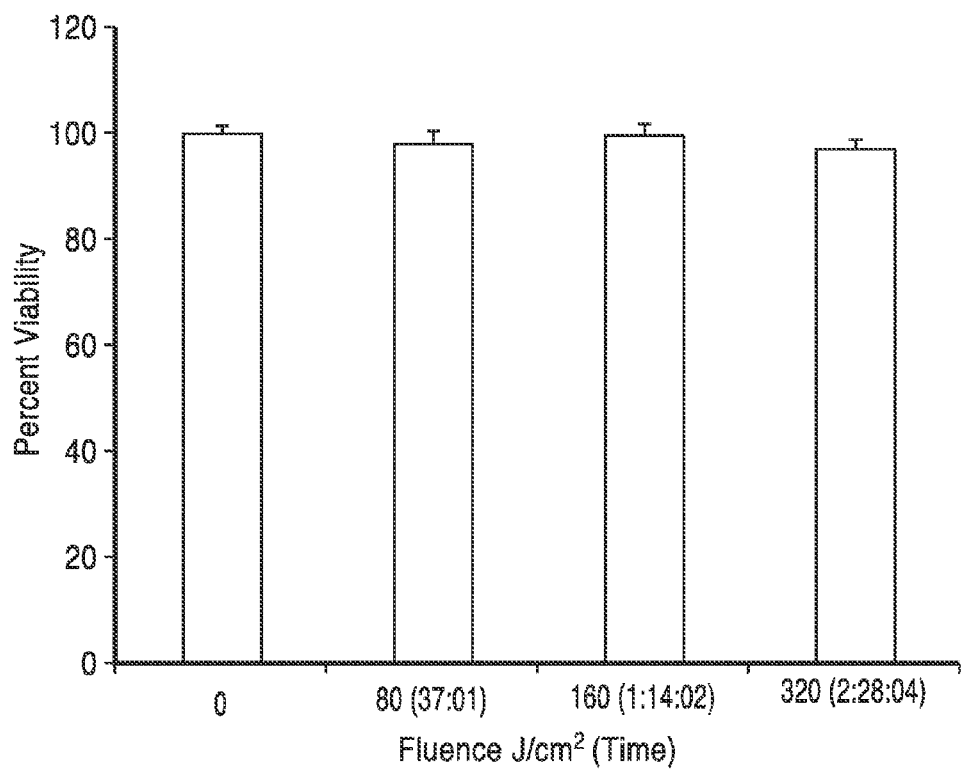
FIG. 10 is a plot showing the effect of LED-Infrared on normal human skin fibroblast viability.

FIG. 10 shows that cellular viability is maintained in normal human skin fibroblasts treated using light-emitting-diode (LED)-generated infrared (IR) light (830 nm). Viability ranged from 97.5±2.0% to 99.8±2.0%. No statistically significant differences were found.

In a third set of experiments, the effects of low-level blue light on fibroblast proliferation were measured.

Figure 11:
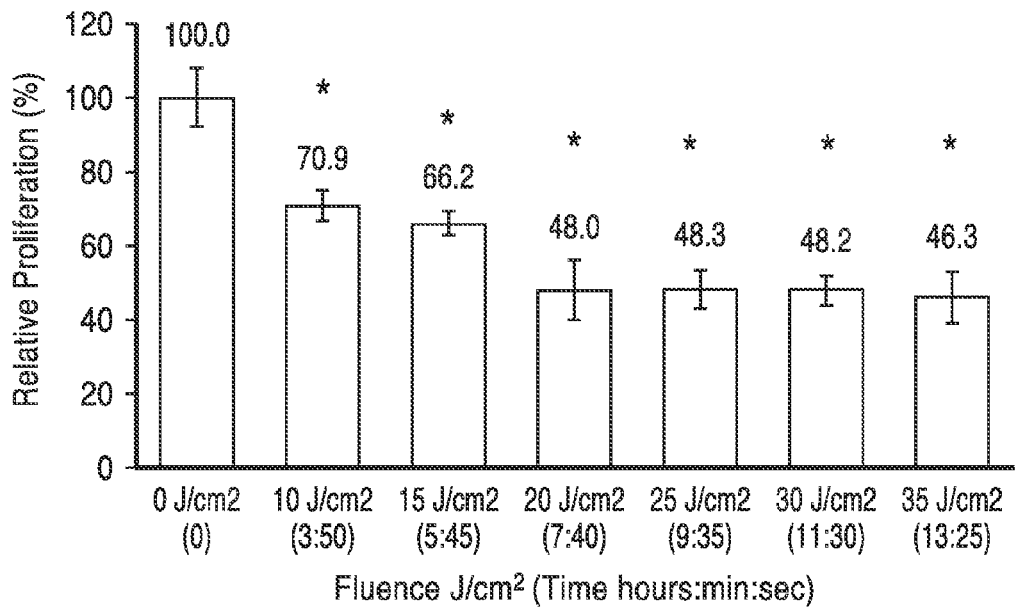
FIG. 11 is a plot showing the effect of LED-Blue Light on Normal human skin fibroblast proliferation.

As seen in FIG. 11, light-emitting-diode (LED) generated blue light (LED-BL) (at 415 nm) significantly decreases the relative proliferation rate of normal human skin fibroblasts at much lower fluences of 0 J/cm$^2$ (0)=100±8%, 10 J/cm$^2$ (3:50)=70.9±4% (p=0.001), 15 J/cm$^2$ (5:45)=66.2±3.1% (p=0.00013), 20 J/cm2 (7:40)=48 ±7.8% (p=0.00014), 25 J/cm$^2$ (9:35)=48.3±5.2% (p=0.00018), 30 J/cm$^2$ (11:30) =48.2±3.7% (p=0.000005), 35 J/cm$^2$ (13:25)=46.3±6.8% (p=0.00002), (p=0.00000647) compared to matched bench control plates. Measurements were also made at 5 J/cm2 (1:55)=91.6 ±3.7% (p=0.75), and at 80 J/cm2 (30:40) =44.9±3.1% (p=0.00000647) (both not shown in FIG. 11). Measurements were assessed using Trypan blue assay. Proliferation shown as percentage of control. Error bars represent standard error of the mean (*p<0.01).

Figure 12:
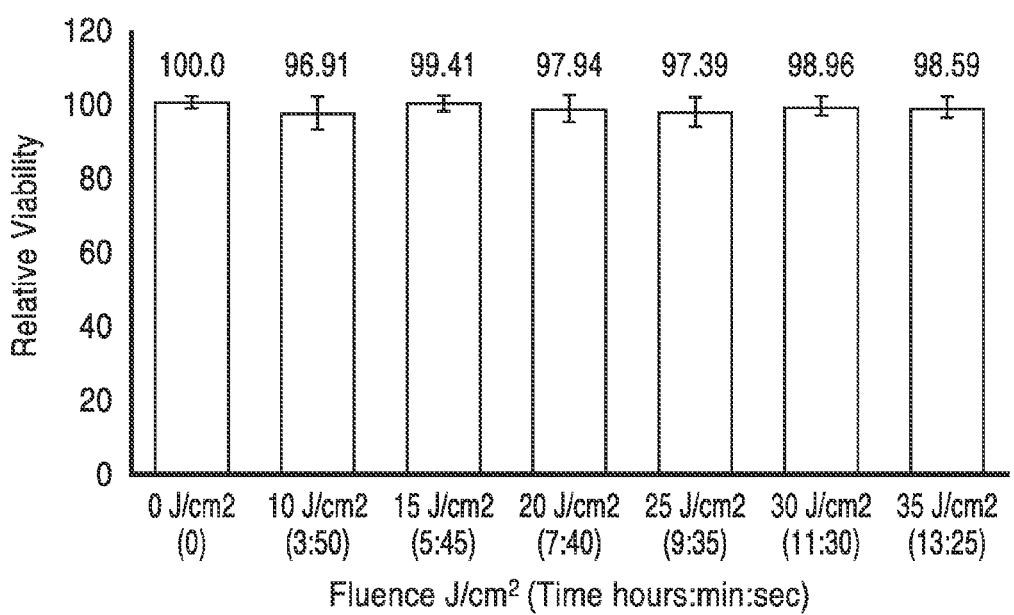
FIG. 12 is a plot showing the effect of LED-Blue Light on normal human skin fibroblast.

Referring to FIG. 12, cellular viability is maintained in normal human skin fibroblasts treated using light-emitting diode (LED)-generated blue light at a wavelength of 415 nm. Viability ranged from 96.91±4.5% to 99.41±2.0% for various fluences.

In conclusion, the above experiments show the following:
1. Preferable wavelengths and the amount of dosage for all wavelengths:
  (a) Red light: 633 nm+/−30 nm; doses tested 5 J/cm$^2$ to 800 J/cm$^2$.
  (b) IR: 830 nm+/−30 nm; doses tested 5 J/cm$^2$ to 640 J/cm$^2$.
  (c) Blue: 415 nm+/−30 nm; doses tested 5 J/cm$^2$ to 80 J/cm$^2$
2. Best/optimum wavelengths and the amount of dosage for all wavelengths:
  (a) Red light: 633 nm+/−30 nm; doses 320 J/cm$^2$, 640 J/cm$^2$, to 800 J/cm$^2$.
  (b) IR: 830 nm+/−30 nm doses; 80 J/cm$^2$ to 320 J/cm$^2$.
  (c) Blue: 415 nm+/−30 nm; 5 J/cm$^2$ to 80 J/cm$^2$.

Based on the investigation described herein, usable wavelengths and amount dosage for various wavelengths are:
  (a) Blue (low spectrum visible light): 400 nm to 500 nm; doses 5 J/cm$^2$ to 3200 J/cm$^2$.
  (b) Red (high spectrum visible light): 585 nm to 700 nm; doses 30 J/cm$^2$ to 3200 J/cm$^2$.
  (b) IR: 700 nm to 2500 nm; doses 30 J/cm$^2$ to 3200 J/cm$^2$.

While the above ranges are preferred, it is appreciated that other wavelengths in the visible spectrum may also be used. Low level light therapy (LLLT) generated by light emitting diodes (LED) holds promise as a non-invasive treatment option for scars. This approach has many clinical advantages compared to other scar therapeutics: it is typically painless, relatively inexpensive, can cover larger treatment areas at a time, does not require highly trained personnel and has superior portability, therefore allowing for patient home use.

These data provide an in vitro correlate to clinical observations and therefore may provide in vitro foundation for further research and translation into therapeutic strategies for scars and other hyperproliferative skin diseases. Skin fibrosis occurs in the dermis, and it is well established that blue light penetrates up to 2 mm, red light penetrates up to 4 mm, and IR penetrate 4 meters and beyond to the mid- to deep dermis. Table 1 shows a list of clinical applications of low-light therapy methods of the present invention may be used to treat various fibrotic disorders.

In the experiments presented above, control was emphasized for environmental conditions by using bench controls, monitored to confirm no supra-physiologic temperatures were induced, and all experiments were repeated to account for variation in cellular proliferation patterns. It is important to note that the experiments were conducted using normal human skin fibroblasts in vitro.

Use of LEDs for LLLT of scars and other proliferative skin diseases is an attractive treatment option to dermatologic surgeons, dermatologists and other medical practitioners, due to the suggested safety profile of LEDs, relatively low cost, portability of LEDs and potential for home use. Additionally, there are minimal side effects associated with LED LLLT, the most common being temporary generation of heat in tissues during treatment. The safety of LEDs for LLLT is supported by our data that demonstrates minimal effect of LED LLLT on cellular viability at fluences that are effective in inhibiting fibroblast proliferation (see FIG. 3, FIG. 6, FIG. 10 and FIG. 12).

Our findings demonstrate the anti-proliferative effect of LED generated red, blue and IR light in vitro. It is proposed that elucidating the cellular and mechanistic effects of LLLT on fibroblasts will contribute to the development of optimal light based technologies that can be applied to improving the lives of patients with cosmetically and functionally-impairing scars as well as other proliferative skin conditions.

From the discussion above it will be appreciated that the invention can be embodied in various ways, including but not limited to the following:

1. A method for treating human skin fibroblasts, the method comprising: directing visible light into a target region of skin tissue; and exposing the skin tissue to a therapeutic dose of visible light sufficient to decrease fibroblast proliferation within said target region of skin tissue.

2. A method as in any of the previous embodiments, wherein the therapeutic dose comprises visible light at a wavelength corresponding to red light.

3. A method as in any of the previous embodiments, wherein the red light is delivered at a fluence of at least about 30 $J/cm^2$.

4. A method as in any of the previous embodiments, wherein the red light is delivered at a fluence of at least about 320 $J/cm^2$.

5. A method as in any of the previous embodiments, wherein the red light is delivered at a fluence of at least about 640 $J/cm^2$.

6. A method as in any of the previous embodiments, wherein the therapeutic dose comprises visible light at a wavelength ranging from about 400 nm to about 700 nm and fluences ranging from about 5 $J/cm^2$ to about 3200 $J/cm^2$.

7. A method as in any of the previous embodiments, wherein one or more LED's are used to direct visible light into a target region.

8. A method for treating human skin fibroblasts, the method comprising: directing infrared light into a target region of skin tissue; and exposing the skin tissue to a therapeutic dose of infrared light sufficient to decrease fibroblast proliferation within said target region of skin tissue.

9. A method as in any of the previous embodiments, wherein the infrared light is delivered at a fluence of at least about 30 $J/cm^2$.

10. A method as in any of the previous embodiments, wherein the infrared light is delivered at a fluence of at least about 160 $J/cm^2$.

11. A method as in any of the previous embodiments, wherein the infrared light is delivered at a fluence of at least about 320 $J/cm^2$.

12. A method as in any of the previous embodiments, wherein the therapeutic dose comprises infrared light at a wavelength ranging from about 700 nm to about 2500 nm and a density ranging from about 30 $J/cm^2$ to about 3200 $J/cm^2$.

13. A method as in any of the previous embodiments, wherein therapeutic dose comprises infrared light at a wavelength of about 830 nm +/−30 nm.

14. A method as in any of the previous embodiments, wherein one or more LED's are used to direct infrared light into a target region.

15. A method for treating human skin fibroblasts, the method comprising: directing visible red light into a target region of skin tissue; and exposing the skin tissue to a therapeutic dose of red light sufficient to decrease fibroblast proliferation within said target region of skin tissue.

16. A method as in any of the previous embodiments, wherein the red light is delivered at a density of at least about 30 $J/cm^2$.

17. A method as in any of the previous embodiments, wherein the red light is delivered at a density of at least about 320 $J/cm^2$.

18. A method as in any of the previous embodiments, wherein the red light is delivered at a density of at least about 640 $J/cm^2$.

19. A method as in any of the previous embodiments, wherein the therapeutic dose comprises red light at a wavelength of about 633 nm+/−30 nm.

20. A method as in any of the previous embodiments, wherein one or more LED's are used to direct visible light into a target region.

21. A method for treating human skin fibroblasts, the method comprising: directing visible blue light into a target region of skin tissue; and exposing the skin tissue to a therapeutic dose of blue light sufficient to decrease fibroblast proliferation within said target region of skin tissue.

22. A method as in any of the previous embodiments, wherein the blue light is delivered at a density of at least about 5 $J/cm^2$.

23. A method as in any of the previous embodiments, wherein the blue light is delivered at a density of at least about 10 $J/cm^2$.

24. A method as in any of the previous embodiments, wherein the blue light is delivered at a density of at least about 30 $J/cm^2$.

25. A method as in any of the previous embodiments, wherein the blue light is delivered at a density of at least about 80 $J/cm^2$ 26. A method as in any of the previous embodiments, wherein the therapeutic dose comprises blue light at a wavelength of about 415 nm+/−30 nm.

27. A method as in any of the previous embodiments, wherein the therapeutic dose comprises visible light at a wavelength ranging from about 400 nm to about 500 nm and a density ranging from about 5 $J/cm^2$ and up.

28. A method as in any of the previous embodiments, wherein one or more LED's are used to direct blue light into a target region.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Clinical Applications

| | |
|---|---|
| Scleroderma | lipodermatosclerosis |
| Scleredema | restrictive dermopathy |
| Scleromyxedema | Hutchinson-Gilford progeria |
| Chronic GVHD | Werner syndrome |
| hypertrophic scars | Stiff skin syndrome |
| keloids | PKU |
| Eosinophilic fascitis | Winchester syndrome |
| Generalized morphea | Ataxia-telangiectasia |
| Fibroblastic rheumatism | Huriez-syndrome (sclerodactyly) |
| POEMS syndrome | Silicosis |
| amyloidosis | Mixed connective tissue disease |
| carcinoid syndrome | circumscript scleroderma |
| carcinome en curasse | acrodermatitis chronica atrophicans |
| diabetic cheiroarthropathy | scleredema adultorum Buschke |
| porphyria cutanea tarda | scleredema diabeticorum |
| congenital erythropoietic porphyria | dermatomyositis |
| reflex sympathetic dystrophy | pretibial myexedma |
| spinal cord injury | lichen sclerosus et atrophicus |
| nephrogenic systemic fibrosis | acrogeria |
| eosinophilia-myalgia syndrome | post-radiation fibrosis |
| toxic oil syndrome | linear scleroderma |
| bleomycin-induced | sclerema neonaturum |
| pentazocine, carbidopa-induced | dermatofibrosarcoma protuberans |
| taxanes-induced | lichen myxedematosus |
| vinyl chloride, chlorinated hydrocarbons exposure | Peyronie's disease, polymyositis |

What is claimed is:

1. A method for inhibiting human skin fibroblasts, the method comprising:
   directing a light source at a target region of skin tissue;
   emitting light from the light source at the skin tissue to expose the skin tissue to a therapeutic dose of light having a specified wavelength, density and duration at the target region of skin tissue;
   said specified wavelength corresponding to light restricted to be within the range of 400 nm to 700 nm;
   said specified fluence ranging from 30 J/cm$^2$ to 3200J/cm$^2$ for the specified duration; and
   inhibiting fibroblast proliferation within the target region as a result of the emitted light at said specified wavelength and fluence to therapeutically treat or prevent scars or other proliferative skin diseases within the target region.

2. A method as recited in claim 1, wherein the therapeutic dose comprises visible light at a wavelength restricted to red light.

3. A method as recited in claim 2, wherein the red light is delivered at a fluence ranging from 80 J/cm$^2$ to 3200J/cm$^2$.

4. A method as recited in claim 2, wherein the red light is delivered at a fluence of at least 320 J/cm$^2$.

5. A method as recited in claim 2, wherein the red light is delivered at a fluence of at least 640 J/cm$^2$.

6. A method as recited in claim 1, wherein the therapeutic dose comprises light at a wavelength of 633 nm +/−30 nm delivered at a fluence of at least 320 J/cm$^2$.

7. A method as recited in claim 1, wherein one or more LED's are used to direct visible light into a target region.

8. A method for inhibiting human skin fibroblasts, the method comprising:
   directing a light source at a target region of skin tissue;
   emitting light from the light source at the skin tissue to expose the skin tissue to a therapeutic dose of light having a specified wavelength, density and duration at the target region of skin tissue;
   said specified wavelength restricted to infrared light at a wavelength ranging from 700 nm to 2500 nm;
   said specified fluence ranging from 30 J/cm$^2$ to 3200 J/cm$^2$; and
   inhibiting fibroblast proliferation within the target region as a result of the emitted light at said specified wavelength and fluence to therapeutically treat or prevent scars or other proliferative skin diseases within the target region.

9. A method as recited in claim 8, wherein the infrared light is delivered at a fluence of at least 30 J/cm$^2$.

10. A method as recited in claim 8, wherein the infrared light is delivered at a fluence of at least 160 J/cm$^2$.

11. A method as recited in claim 8, wherein the infrared light is delivered at a fluence of at least 320 J/cm$^2$.

12. A method as recited in claim 8, wherein the therapeutic dose comprises infrared light at a wavelength of 830 nm +/−30 nm delivered at a fluence of at least 80 J/cm$^2$.

13. A method as recited in claim 8, wherein one or more LED's are used to direct infrared light into a target region.

14. A method for treating human skin fibroblasts, the method comprising:
   directing a light source at a target region of skin tissue;
   emitting light from the light source at the skin tissue to expose the skin tissue to a therapeutic dose of light having a specified wavelength, density and duration at the target region of skin tissue;
   said specified wavelength restricted to visible red light; and
   said specified fluence ranging from 30J/cm$^2$ to 3200 J/cm$^2$ for the specified duration; and
   inhibiting fibroblast proliferation within the target region as a result of the emitted light at said specified wavelength and fluence to therapeutically treat or prevent scars or other proliferative skin diseases within the target region.

15. A method as recited in claim 14, wherein the red light is delivered at a fluence ranging from 320 J/cm$^2$ to 800 J/cm$^2$.

16. A method as recited in claim 14, wherein the red light is delivered at a fluence of at least 320 J/cm$^2$.

17. A method as recited in claim 14, wherein the red light is delivered at a fluence of at least 640 J/cm$^2$.

18. A method as recited in claim 14, wherein the therapeutic dose comprises red light at a wavelength of 633 nm +/−30 nm.

19. A method as recited in claim 14, wherein one or more LED's are used to direct visible light into a target region.

* * * * *